(12) United States Patent
Marshall et al.

(10) Patent No.: US 8,318,665 B1
(45) Date of Patent: *Nov. 27, 2012

(54) CYTOKINE CONTAINING COMPOSITIONS

(75) Inventors: Vivienne S Marshall, San Antonio, TX (US); Catherine J Trumpower, Pittsburgh, PA (US); Charlotte A Smith, Gibsonia, PA (US)

(73) Assignee: Stemnion, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/596,244

(22) Filed: Aug. 28, 2012

Related U.S. Application Data

(62) Division of application No. 13/442,943, filed on Apr. 10, 2012, now Pat. No. 8,278,417, and a division of application No. 13/373,458, filed on Nov. 15, 2011, now Pat. No. 8,198,239, and a division of application No. 12/658,122, filed on Feb. 3, 2010, now Pat. No. 8,088,732, and a division of application No. 12/228,043, filed on Aug. 8, 2008, now abandoned.

(60) Provisional application No. 61/125,960, filed on Apr. 30, 2008, provisional application No. 60/965,707, filed on Aug. 22, 2007.

(51) Int. Cl.
*A61K 38/18* (2006.01)
*A61K 38/22* (2006.01)
*A61K 31/74* (2006.01)

(52) U.S. Cl. ............ 514/5.1; 514/8.2; 514/8.9; 514/9.6; 424/78.31

(58) Field of Classification Search .................. None
See application file for complete search history.

(56) References Cited

U.S. PATENT DOCUMENTS

| 5,612,028 | A  | 3/1997  | Sackier et al. |
| 2003/0191061 | A1 | 10/2003 | Brewitt |
| 2004/0166100 | A1 | 8/2004  | Elia |
| 2004/0228853 | A1 | 11/2004 | Serhan et al. |
| 2006/0222634 | A1 | 10/2006 | Clarke et al. |
| 2007/0231297 | A1 | 10/2007 | Smith et al. |

FOREIGN PATENT DOCUMENTS

WO    WO2006019357 A1 *   2/2006

OTHER PUBLICATIONS

Mclaren et al. (1996), Vascular endothelial growth factor (VEGF) concentration are leevated inperitoneal fluid of women with endometriosis, Hum. Reprod. vol. 11, No. 1, pp. 220-223.*
Bezemer et al. (2000), Microsperes for protein delivery prepared from amphiphilic multiblcok copolymers, J. Cont. Release, vol. 67, pp. 233-248.*
Chemicon Internation, Human TIMP-1 Immunoassay Kit (2000).*
Steed, D., et al., ePlasty 2008, vol. 8, E-location: e18.
Franz, M.G., et al., ePlasty 2008, vol. 8, E-location: e18.
Payne, W.G., et al., World J Surg, published online Feb. 3, 2010, DOI 10.1007/s00268-010-0420-9.

* cited by examiner

*Primary Examiner* — Christine J Saoud
*Assistant Examiner* — Jegatheesan Seharaseyon
(74) *Attorney, Agent, or Firm* — Linda O. Palladino; Gail M. Kempler

(57) ABSTRACT

The invention is directed to novel cellular factor-containing solution compositions (referred to herein as "CFS" compositions), including novel sustained-release cellular factor-containing solution compositions (referred to herein as "SR-CFS" compositions), methods of making such novel compositions and uses thereof.

9 Claims, No Drawings

CYTOKINE CONTAINING COMPOSITIONS

FIELD OF THE INVENTION

The field of the invention is directed to novel cellular factor-containing solution compositions (referred to herein as "CFS" compositions), including novel sustained-release cellular factor-containing solution compositions (referred to herein as "SR-CFS" compositions), methods of making such novel compositions and uses thereof.

BACKGROUND OF THE INVENTION

Many individual cytokines and growth factors have been evaluated for their therapeutic utility in the treatment of many varied diseases, disorders and injuries. Unfortunately, the results have been only partially encouraging. For example, PDGF-BB has proven to be useful in the treatment of diabetic foot ulcers; GM-CSF is marketed in Europe for both venous ulcers and diabetic foot ulcers; and HGH (human growth hormone) is marketed in the US for pediatric burns. Failures include BDNF, CNTF and IGF-1 which have all been evaluated in clinical trials designed to test their efficacy in treating ALS, each with disappointing results; TGFβ2 was unsuccessful in a phase 2 study for venous ulcers; and IGF-1 and PDGF combination therapy was unsuccessful in diabetic foot ulcers.

While is not clear why so many of these individual cytokines and growth factors have failed in the clinic, one theory is that the proteins were being administered in doses that were not physiologic, i.e. very high doses compared to the physiologic levels normally found in vivo. Also, because of the complex interaction between cytokines and growth factors in a given physiological niche, the application of just one factor, especially one at abnormally high levels, cannot recreate the physiological niche and may, in fact, grossly disturb its delicate balance.

Compounding their limited success in the clinic, cytokines and growth factors and other protein-based therapeutics are typically more difficult to administer to patients than other pharmaceuticals. Because the efficacy of a protein is related to its shape, protein-based therapeutics cannot be subjected to conditions that could cause the unfolding, or denaturing, of the protein or proteins contained therein. Consequently, special care is necessary in the preparation, storage, and administration of protein-based therapeutics.

In addition to avoiding any denaturation of the protein, it is often desirable to be able to control the amount of the protein administered to a patient over time. This helps to avoid protein concentrations within the patient that are undesirably high or low or that fluctuate too much from a desired level, and instead helps maintain a steady level of the therapeutic in the patient. To address this, sustained-release formulations for many therapeutics, including protein-based therapeutics, have been or are currently in development. Sustained-release protein-based therapeutics can be administered by a variety of methods, including but not limited to oral delivery of tablets or capsules, inhalation of powders, implantation, incorporation into a matrix, or topical application of an encapsulated therapeutic from which the protein is gradually released over time.

The preparation of such sustained-release formulations are varied. One process includes mixing the protein with an organic solvent. For example, a powder formulation may be made by spraying a mixture of the protein and an organic solvent into liquid nitrogen. Another process involves mixing the protein with a solution of a bioerodible/biodegradable polymer in an organic solvent, resulting in the formation of microparticles which contain the protein and the polymer by coagulation of the mixture. In yet another process, proteins, powdered formulations, or microparticles can be mixed with an organic solvent to produce a liquid or gel which may be injected into a patient or applied topically. Unfortunately, drawbacks to using organic solvents are their tendency to cause protein denaturation.

Additives have been used to stabilize proteins in the presence of a denaturing organic solvent. These additives include surfactants (see U.S. Pat. No. 5,096,885), amino acids (see U.S. Pat. No. 4,297,344), polyols (see U.S. Pat. No. 5,589,167), natural polymers (see WO 8903671), synthetic polymers (see Pharm. Res. 8:285 291, 1991), and metals (see U.S. Pat. No. 6,191,107 B1), each of which is incorporated herein by reference.

To date, no protein-based therapeutic agent (i.e. cytokines and growth factors) is available that effectively recreates or mimics the complex combination and physiologic levels of physiologically relevant cytokines and growth factors found naturally in the body in healthy and disease or injury states. Every protein-based therapeutic currently available administers a dose many, many times higher than the levels that the cytokines or growth factors are normally found in the body. In addition, no one has yet been able to administer these physiologically relevant cytokines and growth factors at physiological levels. Further, no one has yet been able to administer these physiologically relevant cytokines and growth factors at physiological levels in a sustained-release formulation. Therefore, Applicants present herewith for the first time the instant invention whose object is to satisfy the unmet medical need of providing physiologically relevant growth factors and cytokines at physiologic levels (CFS compositions), and in some instances, delivering those physiologically relevant growth factors and cytokines at physiologic levels using a sustained-release formulation (SR-CFS compositions).

BRIEF SUMMARY OF THE INVENTION

It is an object of the instant invention to provide novel cellular factor-containing solution (CFS) compositions that recreate the complex and unique combination and physiologic levels of such cytokines and growth factors found in biological niches. It is further an object of the instant invention to provide novel sustained-release cellular factor-containing solution (SR-CFS) compositions that contain the complex and unique combination and physiologic levels of the cytokines and growth factors found naturally in biological niches. Because the cellular factors are present in levels comparable to physiological levels found in the body, they are optimal for use in therapeutic applications which require intervention to support, initiate, replace, accelerate or otherwise influence biochemical and biological processes involved in the treatment and/or healing of disease and/or injury. In the case of the SR-CFS compositions, the cellular factors are released slowly over time to provide a continual, consistent physiologic level of such factors to optimize healing and/or recovery.

In addition to the novel CFS compositions described herein, it is also an object of the invention to provide methods for making such novel CFS compositions, including pooling cell-derived compositions (i.e. pooled-ECS and pooled-ACCS compositions), and SR-CFS compositions, as well as therapeutic uses thereof.

The pooled cell-derived compositions possess several important properties and characteristics including decreased variability in the levels of physiologically relevant cellular factors necessary for therapeutic effect as compared to non-pooled compositions. The cellular factors are present in levels comparable to physiological levels found in the body and are thus optimal for use in therapeutic applications which require intervention to support, initiate, replace, accelerate or otherwise influence biochemical and biological processes involved in the treatment and/or healing of disease and/or injury. The novel methods described herein of pooling cell-derived compositions to decrease variability has the effect of optimizing levels of the secreted factors such that their full therapeutic potential can be achieved in every pool. In addition to the therapeutic value of such pooled compositions, the method of pooling samples to decrease non-pooled composition-to-composition variability has the significant commercial advantages of increasing production yields by minimizing non-pooled composition rejection for failure to meet product specifications and, consequently, decreasing production costs and increasing revenues.

Accordingly, a first aspect of the invention is an extraembryonic cell-derived cellular cytokine solution composition comprising physiologic concentrations of a) at least one factor selected from VEGF, TGFβ2, Angiogenin and PDGF; and b) at least one MMP inhibitor. In another embodiment the composition of aspect one comprises physiologic concentrations of a) at least two factors selected from VEGF, TGFβ2, Angiogenin and PDGF; and b) at least one MMP inhibitor. In another embodiment the composition of aspect one comprises physiologic concentrations of a) at least three factors selected from VEGF, TGFβ2, Angiogenin and PDGF; and b) at least one MMP inhibitor. In a specific embodiment the MMP inhibitor is selected from TIMP-1 and TIMP-2. In yet another embodiment the composition of aspect one comprises physiologic concentrations of VEGF, TGFβ2, Angiogenin, PDGF and TIMP-1. In still another embodiment the composition of aspect one comprises physiologic concentrations of VEGF, TGFβ2, Angiogenin, PDGF and TIMP-2. In a specific embodiment the composition of aspect one comprises physiologic concentrations of VEGF, TGFβ2, Angiogenin, PDGF, TIMP-1 and TIMP-2.

Aspect two of the invention is one wherein the extraembryonic cell-derived cellular cytokine solution is amnion-derived cellular cytokine solution. In a specific embodiment of aspect two the amnion-derived cellular cytokine solution comprise physiologic concentrations of VEGF, TGFβ2, Angiogenin, PDGF, TIMP-1 and TIMP-2.

Aspect three of the invention is a sustained-release composition comprising the extraembryonic cell-derived cellular cytokine solution of aspect one or the amnion-derived cellular cytokine solution of aspect two.

Aspect four of the invention is a method of making an amnion-derived cellular cytokine solution comprising a) isolating amnion epithelial cells from the amnion of a placenta, b) selecting AMP cells from the amnion epithelial cells, c) culturing the AMP cells until they reach confluence, d) changing the culture medium, e) culturing the cells in the medium, and f) collecting the culture medium of step (e) to obtain amnion-derived cellular cytokine solution. In a particular embodiment of aspect four, step (f) is repeated a plurality of times and the amnion-derived cellular cytokine solution obtained in each step (f) is combined to create a pooled amnion-derived cellular cytokine solution.

Aspect five of the invention is the amnion-derived cellular cytokine solution made by the method of aspect four. In one embodiment, the amnion-derived cellular cytokine solution of aspect five is one wherein the solution comprises the factors VEGF, TGFβ2, Angiogenin, PDGF, TIMP-1 and/or TIMP-2 at physiological concentrations. In certain embodiments of the compositions of the invention, the physiologic concentration is ~5.0-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2.

Aspect six of the invention is a physiologic cytokine solution composition comprising a therapeutic component consisting essentially of physiologic concentrations of: a) one or more factors selected from VEGF, TGFβ2, Angiogenin and PDGF; b) at least MMP inhibitor; and c) a carrier, wherein the physiologic concentration is ~5.0-16 ng/mL for VEGF, ~3.5-4.5 ng/mL for Angiogenin, ~100-165 pg/mL for PDGF, ~2.5-2.7 ng/mL for TGFβ2, and wherein the carrier is normal saline, PBS, lactated Ringer's solution or cell culture medium. In one embodiment of aspect six the MMP inhibitor is TIMP-1 and/or TIMP-2 and the physiologic concentration is ~0.68 µg mL for TIMP-1 and ~1.04 µg/mL for TIMP-2. Another embodiment of aspect six comprises a therapeutic component consisting essentially of physiologic concentrations of: a) VEGF, TGFβ2, Angiogenin and PDGF; b) TIMP-1 and/or TIMP-2; and c) a carrier; wherein the physiologic concentration is ~5.0-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2, and wherein the carrier is normal saline, PBS, lactated Ringer's solution or cell culture medium.

Aspect seven of the invention is a physiologic cytokine solution composition comprising a therapeutic component consisting essentially of a composition selected from the group consisting of: Composition A: VEGF and TIMP-1; Composition B: VEGF, Angiogenin and TIMP-1; Composition C: VEGF, Angiogenin, PDGF-BB and TIMP-1; Composition D: VEGF, Angiogenin, PDGF-BB, TGFβ2 and TIMP-1; Composition E: VEGF and TIMP-2; Composition F: VEGF, Angiogenin and TIMP-2; Composition G: VEGF, Angiogenin, PDGF-BB and TIMP-2; Composition H: VEGF, Angiogenin, PDGF-BB, TGFβ2 and TIMP-2; Composition I: VEGF, TIMP-1 and TIMP-2; Composition J: VEGF, Angiogenin, TIMP-1 and TIMP-2; Composition K: VEGF, Angiogenin, PDGF-BB, TIMP-1 and TIMP-2; Composition L: VEGF, Angiogenin, PDGF-BB, TGFβ2, TIMP-1 and TIMP-2; Composition M: Angiogenin and TIMP-1; Composition N: Angiogenin, PDGF-BB and TIMP-1; Composition O: Angiogenin, PDGF-BB, TGFβ2 and TIMP-1; Composition P: Angiogenin and TIMP-2; Composition Q: Angiogenin, PDGF-BB and TIMP-2; Composition R: Angiogenin, PDGF-BB, TGFβ2 and TIMP-2; Composition S: Angiogenin, PDGF-BB, TGFβ2, TIMP-1 and TIMP-2; Composition T: PDGF-BB and TIMP-1; Composition U: PDGF-BB, TGFβ2 and TIMP-1; Composition V: PDGF-BB and TIMP-2; Composition W: PDGF-BB, TGFβ2 and TIMP-2; Composition X: PDGF-BB, TIMP-1 and TIMP-2; and Composition Y: PDGF-BB, TGFβ2, TIMP-1 and TIMP-2; and a carrier, wherein VEGF, Angiogenin, PDGF-BB, TGFβ2, TIMP-1 and TIMP-2 are at ~5-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2, and wherein the carrier is normal saline, PBS, lactated Ringer's solution or cell culture medium.

Aspect eight of the invention is a sustained-release composition comprising the composition of aspects 6 and 7.

Aspect nine of the invention is the sustained-release composition of aspect eight further comprising an agent capable of effecting sustained-release of the extraembryonic cell-derived cellular cytokine solution, wherein the agent is selected from polymers, blended polymers, hyaluronic acid particles, microencapsulation materials or nanoparticles.

Aspect ten of the invention is a method of making a sustained-release composition comprising the steps of combining a cellular factor-containing solution composition with an agent capable of effecting sustained-release of the cellular factor-containing solution composition.

Aspect 11 of the invention is the sustained-release composition made by the method of aspect 10.

DEFINITIONS

As defined herein "isolated" refers to material removed from its original environment and is thus altered "by the hand of man" from its natural state.

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristics of secreting a unique combination of physiologically relevant cytokines in a physiologically relevant temporal manner into the extracellular space or into surrounding culture media and which have not been cultured in the presence of any animal-derived products, making them and cell products derived from them suitable for human clinical use. In one embodiment, the ECS cells secrete at least one cytokine selected from VEGF, Angiogenin, PDGF and TGFβ2 and at least one MMP inhibitor. In a specific embodiment, the MMP inhibitor is selected from TIMP-1 and TIMP-2. In another embodiment, the ECS cells secrete more than one cytokine selected from VEGF, Angiogenin, PDGF and TGFβ2 and more than one MMP inhibitor. In a specific embodiment, the MMP inhibitor is selected from TIMP-1 and TIMP-2. In a preferred embodiment, the ECS cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2. The ECS cells may optionally express Thymosin β4. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety.

As used herein, the term "amnion-derived multipotent progenitor cell" or "AMP cell" means a specific population of ECS cells that are epithelial cells derived from the amnion. In addition to the characteristics described above for ECS cells, AMP cells have the following characteristics. They have not been cultured in the presence of any animal-derived products, making them and cell products derived from them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated AMP cells will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells. AMP cells have previously been described as "amnion-derived cells" (see U.S. Provisional Application Nos. 60/666, 949, 60/699,257, 60/742,067, U.S. Provisional Application Nos. 60/813,759, U.S. application Ser. No. 11/333,849, U.S. application Ser. No. 11/392,892, and PCTUS06/011392, each of which is incorporated herein in its entirety).

By the term "animal-free" when referring to certain compositions, growth conditions, culture media, etc. described herein, is meant that no animal-derived materials, such as animal-derived serum, other than clinical grade human materials, such as recombinantly produced human proteins, are used in the preparation, growth, culturing, expansion, storage or formulation of the certain composition or process.

By the term "serum-free" when referring to certain compositions, growth conditions, culture media, etc. described herein, is meant that no animal-derived serum (i.e. no non-human) is used in the preparation, growth, culturing, expansion, storage or formulation of the certain composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from ECS cells, including AMP cells.

As used herein, the term "cellular factor-containing solution" or "CFS" composition means a composition having physiologic concentrations of one or more factors selected from VEGF, Angiogenin, PDGF and TGFβ2 and at least one MMP inhibitor. Examples of suitable MMP inhibitors include but are not limited to TIMP-1 and TIMP-2. CFS compositions include conditioned media derived from ECS cells, amnion-derived cellular cytokine solution compositions (see definition below), physiologic cytokine solution compositions (see definition below), and sustained release formulations of such CFS compositions.

As used herein, the term "amnion-derived cellular cytokine solution" or "ACCS" means conditioned medium that has been derived from AMP cells or expanded AMP cells. Amnion-derived cellular cytokine solution or ACCS has previously been referred to as "amnion-derived cytokine suspension".

As used herein, the term "physiologic cytokine solution" or "PCS" composition means a composition which is not cell-derived and which has physiologic concentrations of one or more factors selected from VEGF, Angiogenin, PDGF and TGFβ2 and at least one MMP inhibitor. Examples of suitable MMP inhibitors include but are not limited to TIMP-1 and TIMP-2.

As used herein, the term "suspension" means a liquid containing dispersed components, i.e. cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases.

The term "physiologic" or "physiological level" as used herein means the level that a substance in a living system is found and that is relevant to the proper functioning of a biochemical and/or biological process.

As used herein, the term "pooled" means a plurality of compositions that have been combined to create a new composition having more constant or consistent characteristics as compared to the non-pooled compositions. For example, pooled ACCS has more constant or consistent characteristics compared to non-pooled ACCS. Examples of pooled compositions include "SP pools" (more than one ACCS collection/one placenta), "MP1 pools" (one ACCS collection/placenta, multiple placentas), and "MP2 pools" (more than one ACCS collection/placenta, multiple placentas).

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

The term "therapeutically effective amount" means that amount of a therapeutic agent necessary to achieve a desired physiological effect (i.e. accelerate wound healing).

As used herein, the term "pharmaceutically acceptable" means that the components, in addition to the therapeutic agent, comprising the formulation, are suitable for administration to the patient being treated in accordance with the present invention.

As used herein, the term "therapeutic component" means a component of the composition which exerts a therapeutic benefit when the composition is administered to a subject.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time release capsules and the like.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal injection or infusion.

The terms "sustained-release", "extended-release", "time-release", "controlled-release", or "continuous-release" as used herein means an agent, typically a therapeutic agent or drug, that is formulated to dissolve slowly and be released over time.

The terms "bioerodable" or "bioerosion" as used herein mean a combination of physical (i.e. dissolution) and chemical (i.e. chemical bond cleavage) processes that result in the breakdown of a substance.

The term "biodegradable" or "biodegradation" as used herein means a biological agent (i.e. an enzyme, microbe or cell) is responsible for the breakdown of a substance.

The terms "bioresporbable" or "bioabsorptable" as used herein mean the removal of a breakdown product by cellular activity (i.e. phagocytosis).

As used herein, the term "nanoparticle" means particles of less than 100 nm in diameter that exhibit new or enhanced size-dependent properties compared with larger particles of the same material.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model for wound healing" refers to any art-accepted animal model for wound healing in which the compositions of the invention exhibit efficacy as measured by accelerated wound healing. Non-limiting examples of suitable models are described in Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990; Del-Becarro, et al: The use of specific thromboxane inhibitors to preserve the dermal microcirculation after burning. Surgery 87: 137-141, 1980; Robson, et al: Increasing dermal perfusion after burning by decreasing thromboxane production. J Trauma 20: 722-725, 1980; Polo, et al: An in vivo model of human proliferative scar. J Surg Res 74: 187-195, 1998.). Skilled artisans are aware of other suitable models.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Obtaining and Culturing of Cells

ECS cells—Various methods for isolating cells from the extraembryonic tissue, which may then be used to produce the ECS cells of the instant invention are described in the art (see, for example, US2003/0235563, US2004/0161419, US2005/0124003, U.S. Provisional Application Nos. 60/666, 949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179).

Identifying ECS cells—Once extraembryonic tissue is isolated, it is necessary to identify which cells in the tissue have the characteristics associated with ECS cells (see definition above). For example, cells are assayed for their ability to secrete a unique combination of cytokines into the extracellular space or into surrounding culture medium. Suitable cells are those in which the cytokine or cytokines occurs in the physiological range of ~5.0-16 ng/mL for VEGF, ~3.5-4.5 ng/mL for Angiogenin, ~100-165 pg/mL for PDGF, ~2.5-2.7 ng/mL for TGFβ2, ~0.68 μg/mL for TIMP-1 and ~1.04 μg/mL for TIMP-2. Suitable cells may optionally secrete Thymosin β4.

AMP cells—In a particular embodiment, AMP cell compositions are prepared using the steps of a) recovery of the amnion from the placenta, b) dissociation of the amnion epithelial cells from the amniotic membrane, c) isolating AMP cells from the amnion epithelial cells, d) culturing of the AMP cells in a basal medium with the addition of a naturally derived or recombinantly produced human protein; and optionally d) further proliferation of the cells using additional additives and/or growth factors. Details are contained in US Publication No. 2006-0222634-A1, which is incorporated herein by reference.

AMP cells are cultured as follows: The AMP cells are cultured in a basal medium. Such medium includes, but is not limited to, EPILIFE® (Cascade Biologicals), OPTI-PRO™, VP-SFM serum-free culture medium, IMDM highly enriched basal medium, Advanced DMEM, KNOCKOUT™ DMEM, 293 SFM II defined serum-free medium (all made by Gibco; Invitrogen), HPGM hematopoietic progenitor growth medium, Pro 293S-CDM serum-free medium, Pro 293A-CDM serum-free medium, UltraMDCK™ serum-free medium, UltraCulture™ (all made by Cambrex), STEML1NE® I T-cell expansion medium and STEML1NE® II hematopoietic stem cell expansion medium (both made by Sigma-Aldrich), DMEM, DMEM/F-12 nutrient mixture growth medium, Ham's F 12 nutrient mixture growth medium, M 199 basal culture medium, and other comparable basal media. Such media may optionally contain clinical grade human protein or be supplemented with human clinical grade protein. As used herein a "human protein" is one that is produced naturally or one that is produced using recombinant technology. In certain specific embodiments, "human protein" also is meant to include a human fluid or derivative or preparation thereof, such as human serum or amniotic fluid, which contains human protein.

In a most preferred embodiment, the cells are cultured using a system that is free of animal products to avoid xeno-contamination. In this embodiment, the culture medium is STEMLINE® I T-cell expansion medium and STEMLINE® II hematopoietic stem cell expansion medium, OPTI-PRO™, IMDM highly enriched basal medium or DMEM, and is optionally supplemented with clinical grade human albumin added up to concentrations of 10%. In preferred embodiments, the medium is serum-free in addition to being animal-flee.

Optionally, other factors are used. In one embodiment, epidermal growth factor (EGF) at a concentration of between 0-1 μg/mL is used. In a preferred embodiment, the EGF concentration is around 10 ng/mL. Alternative growth factors which may be used include, but are not limited to, TGFα or TGFβ2 (5 ng/mL; range 0.1-100 ng/mL), activin A, cholera toxin (preferably at a level of about 0.1 μg/mL; range 0-10 μg/mL), transferrin (5 μg/mL; range 0.1-100 μg/mL), fibroblast growth factors (bFGF 40 ng/mL (range 0-200 ng/mL), aFGF, FGF-4, FGF-8; (all in range 0-200 ng/mL), bone morphogenic proteins (i.e. BMP-4) or other growth factors known to enhance cell proliferation. All supplements are clinical grade.

Generation of Cellular Factor-Containing Solution Conditioned Medium

Generation of ECS conditioned medium—is obtained as described below for ACCS, except that ECS cells are used.

Generation of ACCS—The AMP cells of the invention can be used to generate ACCS. In one embodiment, the AMP cells are isolated as described herein and $1 \times 10^6$ cells/mL are seeded into T75 flasks containing between 5-30 mL culture medium, preferably between 10-25 mL culture medium, and most preferably about 10 mL culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention.

It is also contemplated by the instant invention that the ACCS be cryopreserved following collection. It is also contemplated by the invention that ACCS be lyophilized following collection. It is also contemplated by the invention that ACCS be formulated for sustained-release following collection. It is also contemplated that ACCS production be scaled up for generation of sufficient product for clinical testing and for commercialization. Skilled artisans are familiar with cryopreservation lyophilization, and sustained-release formulation methodologies.

It is also contemplated by the invention that CFS compositions such as ACCS and pooled ACCS, be diluted with appropriate diluent prior to use. Appropriate diluents include, without limitation, normal saline, PBS, lactated Ringer's solution, cell culture media, conditioned cell culture media, water, and the like. Such dilutions may be 1:2, 1:3, 1:4, 1:5, 1:10, 1:100, etc. In addition, dilutions may be less than 1:2 (i.e. 1:1, 1:0.5, etc.) The appropriate dilution required will be dependent upon the intended use and therefore will need to be empirically determined by skilled artisans.

The CFS compositions of the invention, including ACCS, pooled ACCS, PCS, etc., are characterized by assaying for physiologically relevant cytokines in the physiologically relevant range of ~5-16 ng/mL for VEGF, ~3.5-4.5 ng/mL for Angiogenin, ~100-165 pg/mL for PDGF, ~2.5-2.7 ng/mL for TGFβ2, ~0.68 μg mL for TIMP-1 and ~1.04 μg/mL for TIMP-2. ACCS and pooled ACCS are optionally assayed for the presence of Thymosin β4.

Generation of Physiologic Cytokine Solution (PCS) Compositions

A non-cellular derived form of ACCS (referred to herein as Physiologic Cytokine Solution ("PCS") composition is generated by combining physiological levels of one or more of VEGF, Angiogenin, PDGF, TGFβ2, and one or more MMP inhibitor (i.e. TIMP-1 and/or TIMP-2) in a carrier. Optionally, the PCS contains Thymosinβ4. The physiological levels for these cytokines are the same as those found in ACCS. Suitable carriers include normal saline, PBS, lactated Ringer's solution, cell culture medium, conditioned cell culture media, water, etc. Such compositions are suitable for cryopreservation, lyophilization, sustained-release formulation, scale-up, and the like. It is contemplated by the present invention that PCS may be produced such that it contains more concentrated levels of the factors than those found in ACCS and that it may be subsequently diluted with appropriate diluent prior to use. Appropriate diluents include, without limitation, normal saline, PBS, lactated Ringer's solution, cell culture media, conditioned cell culture media, water, and the like. Such dilutions may be 1:2, 1:3, 1:4, 1:5, 1:10, 1:100, etc. Such dilutions may also be less than 1:2 (i.e. 1:1, 1:0.5, etc.). The appropriate dilution required will be dependent upon the intended use and therefore will need to be empirically determined by the skilled artisan.

The compositions of the invention can be prepared in a variety of ways depending on their intended use. For example, a composition may be a liquid comprising an agent of the invention, i.e. ACCS, pooled ACCS, and PCS. A liquid composition also includes a gel. The liquid composition may be aqueous or in the form of an ointment, salve, cream, or the like. The liquid composition may also be formulated in such a way as to be suitable for a spray or aerosol application.

A useful aqueous suspension may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or mucoadhesive, or even more preferably, both viscous and mucoadhesive.

Sustained-Release Compositions

The CFS compositions, including but not limited to ACCS, pooled ACCS and PCS, maybe formulated as sustained-release CFS compositions (referred to herein as "SR-CFS"). Skilled artisans are familiar with methodologies to create sustained-release compositions of therapeutic agents, including protein-based therapeutic agents such as ACCS, pooled ACCS or PCS.

SR-CFS, including but not limited to SR-ACCS and SR-PCS, may be made by any of the methods described herein. For example, multivesicular liposome formulation technology is useful for the sustained-release of protein and peptide therapeutics. Qui, J., et al, (ACTA Pharmacol Sin, 2005, 26(11):1395-401) describe this methodology for the formulation of sustained-release interferon alpha-2b. Vyas, S. P., et al, (Drug Dev Ind Pharm, 2006, 32(6):699-707) describe encapsulating pegylated interferon alpha in multivesicular liposomes. ACCS (including pooled ACCS) and PCS are suitable for use in multivesicular liposome sustained-release formulation.

Nanoparticle technology is also useful for creating SR-CFS. For example, Packhaeuser, C. B., et al, (J Control Release, 2007, 123(2):131-40) describe biodegradable parenteral depot systems based on insulin loaded dialkylaminoalkyl-amine-poly(vinyl alcohol)-g-poly(lactide-co-glycolide) nanoparticles and conclude that nanoparticle-based depots are suitable candidates for the design of controlled-release devices for bioactive macromolecules (i.e. proteins). Dailey, L. A., et al, (Pharm Res 2003, 20(12):2011-20) describe surfactant-free, biodegradable nanoparticles for aerosol therapy which is based on the branched polymers DEAPA-PVAL-g-PLGA and conclude that DEAPA-PVAL-g-PLGA are versatile drug delivery systems. ACCS (including pooled ACCS) and PCS are suitable for use in nanoparticle-based sustained-release formulations.

Polymer-based sustained-release formulations are also very useful. Chan, Y. P., et al, (Expert Opin Drug Deliv, 2007, 4(4):441-51) provide a review of the Medusa system (Flamel Technologies), which is used for sustained-release of protein and peptide therapies. Thus far, the Medusa system has been applied to subcutaneous injection of IL-2 and IFN-alpha(2b), in animal models (rats, dogs, monkeys), and in clinical trials in renal cancer (IL-2) and hepatitis C (IFN-alpha(2b)) patients. Chavanpatil, M. D., et al, (Pharm Res, 2007, 24(4): 803-10) describe surfactant-polymer nanoparticles as a novel platform for sustained and enhanced cellular delivery of water-soluble molecules. Takeuchi, H., et al, (Adv Drug Deliv Res, 2001, 47(1):39-54) describe mucoadhesive nanoparticulate systems for peptide drug delivery, including liposomes and polymeric nanoparticles. Wong, H. L., et al, (Pharm Res, 2006, 23(7):1574-85) describe a new polymer-lipid hybrid system which has been shown to increase cytotoxicity of doxorubicin against multidrug-resistant breast cancer cells. CFS compositions, including but not limited to ACCS (including pooled ACCS) and PCS are suitable for use in the aforementioned sustained-release formulation methodologies.

In addition, other sustained-release methodologies familiar to skilled artisans, while not specifically described herein, are also suitable for use with the CFS compositions.

Pharmaceutical Compositions of CFS Compositions Including, but not Limited to, ACCS, Pooled ACCS, PCS, SR-ACCS (Including Pooled ACCS), and SR-PCS The present invention provides pharmaceutical compositions of CFS compositions and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits Comprising CFS Compositions Including, but not Limited to, ACCS, Pooled ACCS, PCS, SR-ACCS (Including Pooled ACCS), and SR-PCS The invention also provides for an article of manufacture comprising packaging material and a pharmaceutical composition of the invention contained within the packaging material, wherein the pharmaceutical composition comprises CFS compositions. The packaging material comprises a label or package insert which indicates that the CFS compositions contained therein can be used for therapeutic applications such as, for example, wound healing.

Formulation, Dosage and Administration of CFS Compositions Including, but not Limited to, ACCS, Pooled ACCS, PCS, SR-ACCS (Including Pooled ACCS), and SR-PCS Compositions comprising CFS compositions may be administered to a subject to provide various cellular or tissue functions, for example, to accelerate wound healing. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their therapeutic use. The compositions may also be administered to the recipient in one or more physiologically acceptable carriers. Carriers for CFS compositions may include but are not limited to solutions of normal saline, phosphate buffered saline (PBS), lactated Ringer's solution containing a mixture of salts in physiologic concentrations, or cell culture medium.

In addition, one of skill in the art may readily determine the appropriate dose of the CFS compositions for a particular purpose. A preferred dose is in the range of about 0.1-to-1000 micrograms per square centimeter of applied area. Other preferred dose ranges are 1.0-to-50.0 micrograms/applied area. In a particularly preferred embodiment, it has been found that relatively small amounts of the CFS compositions are therapeutically useful. One exemplification of such therapeutic utility is the ability for ACCS (including pooled ACCS) to accelerate wound healing (for details see U.S. Publication No. 2006/0222634 and U.S. Publication No. 2007/1231297, each incorporated herein by reference). One of skill in the art will also recognize that the number of doses to be administered needs also to be empirically determined based on, for example, severity and type of disease, disorder or injury being treated. For example, in a preferred embodiment, one dose is sufficient to have a therapeutic effect (i.e. accelerate wound healing). Other preferred embodiments contemplate, 2, 3, 4, or more doses for therapeutic effect.

The skilled artisan will recognize that a preferred dose is one which produces a therapeutic effect (a therapeutically effective amount) such as accelerating wound healing, in a patient in need thereof. Of course, proper doses of the CFS compositions will require empirical determination at time of use based on several variables including but not limited to the severity and type of injury, disorder or condition being treated; patient age, weight, sex, health; other medications and treatments being administered to the patient; and the like. One of skill in the art will also recognize that number of doses (dosing regimen) to be administered needs also to be empirically determined based on, for example, severity and type of injury, disorder or condition being treated. In addition, one of skill in the art recognizes that the frequency of dosing needs to be empirically determined based on severity and type of injury, disorder or condition being treated. In certain embodiments, one dose is administered every day for a given number of days (i.e. once a day for 7 days, etc.). In other embodiments, multiple doses may be administered in one day (every 4 hours, etc.). Multiple doses per day for multiple days is also contemplated by the invention.

In further embodiments of the present invention, at least one additional agent may be combined with the CFS compositions. Such agents may act synergistically with the CFS compositions of the invention to enhance the therapeutic effect. Such agents include but are not limited to growth factors, cytokines, chemokines, antibodies, inhibitors, antibiotics, immunosuppressive agents, steroids, anti-fungals, antivirals or other cell types (i.e. stem cells or stem-like cells, for example AMP cells). Inactive agents include carriers, diluents, stabilizers, gelling agents, delivery vehicles, ECMs (natural and synthetic), scaffolds, and the like. When the CFS compositions are administered conjointly with other pharmaceutically active agents, even less of the CFS compositions may be needed to be therapeutically effective.

CFS compositions can be administered by injection into a target site of a subject, preferably via a delivery device, such as a tube, e.g., catheter. In a preferred embodiment, the tube additionally contains a needle, e.g., a syringe, through which the CFS compositions can be introduced into the subject at a desired location. Specific, non-limiting examples of administering the CFS compositions to subjects may also include administration by subcutaneous injection, intramuscular injection, intravenous injection, intraarterial injection, intracardiac injection, intradermal injection, intrathecal injection, epidural injection, intraperitoneal injection, or intracerebral injection. Infusions are also contemplated by the methods of the invention (i.e. subdural, intrathecal or intracerebral infusion). If administration is intravenous, an injectable liquid suspension can be prepared and administered by a continuous drip or as a bolus. In some instances, it may be appropriate to administer the CFS compositions using an infusion pump.

The timing of administration of CFS compositions will depend upon the type and severity of the disease, disorder or injury being treated. In one embodiment, the CFS compositions are administered as soon as possible after the diagnosis or injury. In another embodiment, CFS compositions are administered more than one time following diagnosis or injury. In certain embodiments, where surgery is required, the CFS compositions are administered at surgery. In still other embodiments, the CFS compositions are administered at as well as after surgery. Such post-surgical administration may take the form of a single administration or multiple administrations.

CFS compositions may also be inserted into a delivery device, e.g., a syringe, in different forms. For example, the CFS compositions can be part of a solution contained in such a delivery device. As used herein, the term "solution" includes a pharmaceutically acceptable carrier or diluent. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and may optionally be preserved against the contaminating action of microorganisms such as bacteria and fungi through the use of, for example, parabens, chlorobutanol, phenol, ascorbic acid, thimerosal, and the like. Solutions of the invention can be prepared by incorporating the CFS compositions in a pharmaceutically acceptable carrier or diluent and, as required, other ingredients enumerated above.

CFS compositions may be administered systemically (for example intravenously), locally (for example by direct application under visualization during surgery) or topically. For such administration, the compositions may be in an injectable liquid suspension preparation or in a biocompatible medium which is injectable in liquid form and becomes semi-solid at the site of damaged tissue. A controllable endoscopic delivery device can also be used.

Support matrices into which the CFS compositions can be incorporated or embedded include matrices which are recipient-compatible and which degrade into products which are not harmful to the recipient.

Natural and/or synthetic biodegradable matrices are examples of such matrices. Natural biodegradable matrices include plasma clots, e.g., derived from a mammal, collagen, fibronectin, and laminin matrices. Suitable synthetic matrix material must be biocompatible to preclude immunological complications. It must also be resorbable. The matrix should be configurable into a variety of shapes and should have sufficient strength to prevent collapse upon implantation. Recent studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991)). Other synthetic biodegradable support matrices include synthetic polymers such as polyanhydrides, polyorthoesters, and polylactic acid. Further examples of synthetic polymers and methods of incorporating or embedding compositions into these matrices are also known in the art. See e.g., U.S. Pat. Nos. 4,298,002 and 5,308,701.

One of the advantages of a biodegradable polymeric matrix is that CFS compositions can be incorporated directly into the support matrix so that it is slowly released as the support matrix degrades in vivo. In addition to the CFS compositions, other factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., growth factors such as epidermal growth factor (EGF) and heparin binding epidermal growth factor like growth factor (HB-EGF), could be incorporated into the matrix or be provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792, 525, 5,965,997, 4,879,237 and 4,789,734).

In another example, the CFS compositions may be incorporated in a gel matrix (such as Gelfoam from Upjohn Company). A variety of encapsulation technologies have been developed (e.g. Lacy et al., Science 254:1782-84 (1991); Sullivan et al., Science 252:718-712 (1991); WO 91/10470; WO 91/10425; U.S. Pat. No. 5,837,234; U.S. Pat. No. 5,011, 472; U.S. Pat. No. 4,892,538). During open surgical procedures involving direct physical access to diseased or damaged tissue, all of the described forms of the CFS composition delivery preparations are available options. These compositions can be repeatedly administered at intervals until a desired therapeutic effect, i.e. accelerated wound healing, is achieved.

The three-dimensional matrices to be used are structural matrices that provide a scaffold to guide the process of tissue healing and formation. Scaffolds can take forms ranging from fibers, gels, fabrics, sponge-like sheets, and complex 3-D structures with pores and channels fabricated using complex Solid Free Form Fabrication (SFFF) approaches. As used herein, the term "scaffold" means a three-dimensional (3D) structure (substrate and/or matrix). It may be composed of biological components, synthetic components or a combination of both. Further, it may be naturally constructed by cells or artificially constructed. In addition, the scaffold may contain components that have biological activity under appropriate conditions. The structure of the scaffold can include a mesh, a sponge or can be formed from a hydrogel.

The design and construction of the scaffolding to form a three-dimensional matrix is of primary importance. The matrix should be a pliable, non-toxic, injectable porous template for vascular ingrowth. The pores should allow vascular ingrowth. These are generally interconnected pores in the range of between approximately 100 and 300 microns, i.e., having an interstitial spacing between 100 and 300 microns, although larger openings can be used. The matrix should be shaped to maximize surface area, to allow adequate diffusion of nutrients, gases and growth factors. At the present time, a porous structure that is relatively resistant to compression is preferred, although it has been demonstrated that even if one or two of the typically six sides of the matrix are compressed, that the matrix is still effective to yield tissue growth.

The polymeric matrix may be made flexible or rigid, depending on the desired final form, structure and function. For repair of a defect, for example, a flexible fibrous mat is cut to approximate the entire defect then fitted to the surgically prepared defect as necessary during implantation. An advantage of using the fibrous matrices is the ease in reshaping and rearranging the structures at the time of implantation.

The invention also provides for the delivery of CFS compositions in conjunction with any of the above support matrices as well as amnion-derived membranes. Such membranes may be obtained as a by-product of the process described herein for the recovery of AMP cells, or by other methods, such as are described, for example, in U.S. Pat. No. 6,326,019 which describes a method for making, storing and using a surgical graft from human amniotic membrane, US 2003/ 0235580 which describes reconstituted and recombinant amniotic membranes for sustained delivery of therapeutic molecules, proteins or metabolites, to a site in a host, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. In accordance with the present invention, CFS compositions may be incorporated into such membranes.

Exemplary Therapeutic Uses of CFS Compositions Including, but not Limited to, ACCS, Pooled ACCS, PCS, SR-ACCS (Including Pooled ACCS), and SR-PCS Wound Healing The CFS compositions of the present invention are effective in accelerating wound healing of wounds caused by a number of sources, including but not limited to incisional, compression, thermal, radiation, penetrating, concussive, acute, chronic, infected, and sterile injuries. The instant invention is based upon the discovery that CFS compositions can accelerate the wound healing process for all wound types, particularly when administered topically, i.e. to the surface of the wound site. Using CFS compositions all wound types, mechanical or thermal, acute or chronic, infected or sterile, undergo healing more rapidly than similar wounds left to heal naturally or which are treated with currently available methods. A "therapeutically effective amount" of a therapeutic agent within the meaning of the present invention will be determined by a patient's attending physician or veterinarian. Such amounts are readily ascertained by one of ordinary skill in the art and will enable accelerated wound healing when administered in accordance with the present invention. Factors which influence what a therapeutically effective amount will be include, the specific activity of the therapeutic agent being used, the wound type (mechanical or thermal, full or partial thickness, etc.), the size of the wound, the wound's depth (if full thickness), the absence or presence of infection, time elapsed since the injury's infliction, and the age, physical condition, existence of other disease states, and nutritional status of the patient. Additionally, other medication the patient may be receiving will effect the determination of the therapeutically effective amount of the therapeutic agent to administer.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

Example 1

Preparation of AMP Cell Compositions

Recovery of AMP Cells

AMP cells were dissociated from starting amniotic membrane using the dissociation agents PXXIII, and trypsin. The average weight range of an amnion was 18-27 g. The number of cells recovered per g of amnion was about $10\text{-}15 \times 10^6$ for dissociation with PXXIII and $5\text{-}8 \times 10^6$ for dissociation with trypsin.

Method of obtaining selected AMP cells: Cells were plated immediately upon isolation from the amnion. After ~2 days in culture non-adherent cells were removed and the adherent cells were kept. This attachment to a plastic tissue culture vessel is the selection method used to obtain the desired population of AMP cells. Adherent and non-adherent AMP cells appear to have a similar cell surface marker expression profile but the adherent cells have greater viability and are the desired population of cells. Adherent AMP cells were cultured until they reached ~120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reached ~120,000-150,000 cells/cm$^2$, they were collected and cryopreserved. This collection time point is called p0.

Example 2

Generation of ACCS

The AMP cells of the invention can be used to generate ACCS, including pooled ACCS. The AMP cells were isolated as described above and $\sim 1 \times 10^6$ cells/mL were seeded into T75 flasks containing ~10 mL culture medium. The cells were cultured until confluent, the medium was changed and ACCS was collected 3 days post-confluence. Skilled artisans will recognize that other embodiments for collecting ACCS from confluent cultures, such as using other tissue culture vessels, including but not limited to cell factories, flasks, hollow fibers, or suspension culture apparatus, etc. are also contemplated by the methods of the invention (see Detailed Description above). It is also contemplated by the instant invention that the ACCS be cryopreserved, lyophilized or formulated for sustained-release following collection. It is also contemplated that ACCS be collected at different time point (see Detailed Description for details).

Example 3

Generation of Pooled ACCS

ACCS was obtained essentially as described above. In certain embodiments, ACCS was collected multiple times from an AMP cell culture derived from one placenta and these multiple ACCS collections were pooled together. Such pools are referred to as "SP pools" (more than one ACCS collection/one placenta). In another embodiment, AMP cell cultures were derived from several placentas, i.e. from 5 or 10 placentas. The AMP cells from each placenta were cultured and one ACCS collection from each culture was collected and then they were all pooled. These pools are termed "MP1 pools" (one ACCS collection/placenta, multiple placentas). In yet another embodiment, AMP cell cultures were derived from several placentas, i.e. from 5 or 10 placentas. The AMP cells from each placenta were cultured and more than one ACCS collection was performed from each AMP cell culture and then pooled. These pools are termed "MP2 pools" (more than one ACCS collection/placenta, multiple placentas).

Example 4

Detection of Cytokines in Non-Pooled and Pooled ACCS Using ELISA

Standard ELISAs familiar to skilled artisan are performed on ACCS from AMP cells obtained from 10 different placentas. In addition to assaying each ACCS sample individually, pooled ACCS samples are also tested to determine if variability of ELISA results between samples is reduced. ACCS is obtained as described above. Pools are made as follows: Pool 1 is comprised of ACCS from placentas 1-5, Pool 2 is comprised of ACCS from placentas 6-10, and Pool 3 is comprised of ACCS from placentas 1-10. In addition, ELISA of SP, MP1, MP2 pools is performed.

Example 5

Generation of PCS Compositions

The following PCS compositions are produced by combining the indicated cytokine or factor at physiologic levels in a carrier:
Composition A: VEGF and TIMP-1
Composition B: VEGF, Angiogenin and TIMP-1
Composition C: VEGF, Angiogenin, PDGF-BB and TIMP-1
Composition D: VEGF, Angiogenin, PDGF-BB, TGFβ2 and TIMP-1
Composition E: VEGF and TIMP-2
Composition F: VEGF, Angiogenin and TIMP-2
Composition G: VEGF, Angiogenin, PDGF-BB and TIMP-2
Composition H: VEGF, Angiogenin, PDGF-BB, TGFβ2 and TIMP-2
Composition I: VEGF, TIMP-1 and TIMP-2
Composition J: VEGF, Angiogenin, TIMP-1 and TIMP-2
Composition K: VEGF, Angiogenin, PDGF-BB, TIMP-1 and TIMP-2
Composition L: VEGF, Angiogenin, PDGF-BB, TGFβ2, TIMP-1 and TIMP-2
Composition M: Angiogenin and TIMP-1
Composition N: Angiogenin, PDGF-BB and TIMP-1
Composition O: Angiogenin, PDGF-BB, TGFβ2 and TIMP-1
Composition P: Angiogenin and TIMP-2
Composition Q: Angiogenin, PDGF-BB and TIMP-2
Composition R: Angiogenin, PDGF-BB, TGFβ2 and TIMP-2
Composition S: Angiogenin, PDGF-BB, TGFβ2, TIMP-1 and TIMP-2
Composition T: PDGF-BB and TIMP-1
Composition U: PDGF-BB, TGFβ2 and TIMP-1
Composition V: PDGF-BB and TIMP-2
Composition W: PDGF-BB, TGFβ2 and TIMP-2
Composition X: PDGF-BB, TIMP-1 and TIMP-2
Composition Y: PDGF-BB, TGFβ2, TIMP-1 and TIMP-2
Compositions A-Y optionally contains Thymosin β4. Skilled artisans will recognize that in certain embodiments other MMP inhibitors (i.e. TIMP-3, TIMP-4 or synthetic MMP inhibitors) may be suitable (J. Frederick Woessner, Jr., J. Clin. Invest. 108(6): 799-800 (2001); Brew, K., et al, *Biochim Biophys Acta.* 2000 Mar. 7; 1477(1-2):267-83).

VEGF, Angiogenin, PDGF-BB, TGFβ2, TIMP-1 and TIMP-2 are added at the following physiologic levels: ~5-16 ng/mL for VEGF, ~3.5-4.5 ng/mL for Angiogenin, ~100-165 pg/mL for PDGF, ~2.5-2.7 ng/mL for TGFβ2, ~0.68 μg mL for TIMP-1 and ~1.04 μg/mL for TIMP-2. VEGF may be obtained from Invitrogen, catalog #PHG0144, PHG0145, PHG0146, PHG0141 or PHG0143; Angiogenin may be obtained from R&D Systems, catalog #265-AN-050 or 265-AN-250; PDGF-BB may be obtained from Invitrogen, catalog #PHG0044, #PHG0045, #PHG0046, #PHG0041, #PHG0043; TGFβ2 may be obtained from Invitrogen, catalog #PHG9114; TIMP-1 may be obtained from R&D Systems, catalog #970-TM-010; and TIMP-2 may be obtained from R&D Systems, catalog #971-TM-010. VEGF, Angiogenin, PDGF-BB, TGFβ2, TIMP-1 and TIMP-2 are added to a carrier such as normal saline, PBS, lactated Ringer's solution, cell culture media, water or other suitable aqueous solution known to skilled artisans.

The PCS compositions are tested in standard animal models for wound healing to assess activity (see Definitions above for standard animal models for wound healing).

Example 6

Generation of Sustained-Release CFS Compositions

SR-CFS compositions, such as, for example, SR-ACCS (including pooled ACCS) or SR-PCS, are produced by combining CFS compositions with any of the sustained-release formulation technologies described herein (see Detailed Description) or otherwise familiar to skilled artisans.

Example 7

Effects of ACCS in an Animal Model of Chronic Wound Healing

An art-accepted animal model for chronic granulating wound was used to study the effects of ACCS on chronic wound healing (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990.).

Results: ACCS was effective in not allowing proliferation of tissue bacterial bioburden. ACCS allowed accelerated healing of the granulating wound significantly faster than the non-treated infected control groups.

Example 8

Use of CFS Compositions PCS, SR-ACCS and SR-PCS in an Animal Model of Chronic Wound Healing An art-accepted animal model for chronic granulating wound (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990) is used to study the effects of the CFS compositions PCS, SR-ACCS or SR-PCS of the invention on chronic wound healing.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification

What is claimed is:
1. A composition comprising:
a) a first component consisting of an extraembryonic cell-derived cellular cytokine solution composition comprising physiologic concentrations of VEGF, TGFβ2, Angiogenin, PDGF, TIMP-1 and TIMP-2, wherein the physiologic concentration is ~5.0-16 ng/mL for VEGF, ~3.5-4.5 ng/mL for Angiogenin, ~100-165 pg/mL for

PDGF, ~2.5-2.7 ng/mL for TGFβ2, ~0.68 μg mL for TIMP-1 and ~1.04 μg/mL for TIMP-2; and b) a second component consisting of a matrix, wherein the matrix is selected from the group consisting of a gel, an extracellular matrix, a 3-dimensional scaffold, and a muco-adhesive substance.

2. A composition comprising:

a) a first component consisting of Amnion-derived Cellular Cytokine Solution (ACCS), which comprises physiologic concentrations of VEGF, TGFβ2, Angiogenin, PDGF, TIMP-1 and TIMP-2, wherein the physiologic concentration is ~5.0-16 ng/mL for VEGF, ~3.5-4.5 ng/mL for Angiogenin, ~100-165 pg/mL for PDGF, ~2.5-2.7 ng/mL for TGFβ2, ~0.68 μg mL for TIMP-1 and ~1.04 μg/mL for TIMP-2; and b) a second component consisting of a matrix, wherein the matrix is selected from the group consisting of a gel, an extracellular matrix, a 3-dimensional scaffold, and a muco-adhesive substance.

3. A composition comprising:

a) a first component consisting of a physiologic cytokine solution composition comprising a therapeutic component consisting of physiologic concentrations of:

i) VEGF, TGFβ2, Angiogenin, PDGF, TIMP-1 and TIMP-2; and ii) a carrier, wherein the physiologic concentration is ~5.0-16 ng/mL for VEGF, ~3.5-4.5 ng/mL for Angiogenin, ~100-165 pg/mL for PDGF, ~2.5-2.7 ng/mL for TGFβ2, ~0.68 μg mL for TIMP-1 and ~1.04 μg/mL for TIMP-2, and wherein the carrier is normal saline, PBS, lactated Ringer's solution or cell culture medium; and b) a second component consisting of a matrix, wherein the matrix is selected from the group consisting of a gel, an extracellular matrix, a 3-dimensional scaffold, and a muco-adhesive substance.

4. The composition of claim 1, 2, or 3 wherein the gel is selected from the group consisting of an ointment, a salve, a cream, and a gelfoam.

5. The composition of claim 1, 2, or 3 wherein the extracellular matrix is selected from the group consisting of a natural extracellular matrix and a synthetic extracellular matrix.

6. The composition of claim 5 wherein the natural extracellular matrix is biodegradable and selected from the group consisting of plasma clots, collagen, fibronectin, and laminin.

7. The composition of claim 5 wherein the synthetic extracellular matrix is biodegradable and selected from the group consisting of a polyglycolic acid, a polyanhydride, a polyorthoester, and a polylactic acid.

8. The composition of claim 5 wherein the natural extracellular matrix is an amnion-derived membrane.

9. The composition of claim 1, 2, or 3 wherein the 3-dimensional scaffold is selected from the group consisting of fibers, fabrics, sponge-like sheets, a mesh, and a hydrogel.

* * * * *